(12) United States Patent
Guichet

(10) Patent No.: US 10,080,619 B2
(45) Date of Patent: Sep. 25, 2018

(54) DEFIBRILLATOR STORAGE DEVICE

(71) Applicant: HD1PY, Inc., Tampa, FL (US)

(72) Inventor: Robert Guichet, Canohes (FR)

(73) Assignee: HD1PY, INC., Tampa, FL (US)

( * ) Notice: Subject to any disclaimer, the term of this patent is extended or adjusted under 35 U.S.C. 154(b) by 432 days.

(21) Appl. No.: 14/962,779

(22) Filed: Dec. 8, 2015

(65) Prior Publication Data

US 2016/0166349 A1   Jun. 16, 2016

Related U.S. Application Data

(60) Provisional application No. 62/090,497, filed on Dec. 11, 2014, provisional application No. 62/132,597, filed on Mar. 13, 2015.

(51) Int. Cl.
| | | |
|---|---|---|
| *G08B 13/08* | (2006.01) | |
| *A61B 50/10* | (2016.01) | |
| *A61N 1/39* | (2006.01) | |
| *A61B 50/00* | (2016.01) | |

(52) U.S. Cl.
CPC ...... *A61B 50/10* (2016.02); *A61B 2050/0051* (2016.02); *A61B 2050/105* (2016.02); *A61N 1/39* (2013.01); *A61N 1/3968* (2013.01)

(58) Field of Classification Search
CPC ...... A61N 1/39; A61N 1/3925; A61N 1/3968; A61B 50/10; A61B 2050/105
USPC .......... 340/545, 541, 286.07, 288, 289, 296, 340/301; 607/5
See application file for complete search history.

(56) References Cited

U.S. PATENT DOCUMENTS

| | | | |
|---|---|---|---|
| 6,301,501 B1 | 10/2001 | Cronin et al. | |
| 6,668,192 B1* | 12/2003 | Parker | A61N 1/39 600/522 |
| 6,735,473 B2* | 5/2004 | Kolder | A61N 1/3931 607/5 |
| 7,510,526 B2* | 3/2009 | Merry | A61N 1/39 600/300 |
| 7,570,994 B2* | 8/2009 | Tamura | A61N 1/3975 607/5 |
| 8,220,628 B2* | 7/2012 | Hochhalter | A61N 1/3968 206/363 |
| 2015/0254949 A1* | 9/2015 | Knight | B65B 25/02 340/556 |

FOREIGN PATENT DOCUMENTS

DE  10 2012 0170122 A2 *  2/2014  .......... A61N 1/3968

\* cited by examiner

*Primary Examiner* — Toan N Pham
(74) *Attorney, Agent, or Firm* — Shumaker, Loop & Kendrick, LLP

(57) ABSTRACT

A defibrillator storage device including a housing defining an interior storage compartment configured to hold a removable automated external defibrillator therein, a door pivotally attached to the housing, an alarm disposed within the housing, and a tether attached at a first end thereof to an interior wall of the housing and at a second end thereof to the alarm, the tether configured to be routed through a handle of the automated external defibrillator such that removal of the automated external defibrillator from the interior compartment causes the second end of the tether to be pulled from the alarm, thereby triggering the alarm.

34 Claims, 22 Drawing Sheets

DEFIBRILLATOR STORAGE DEVICE

CROSS-REFERENCE TO RELATED APPLICATIONS

This U.S. Non-Provisional Patent Application claims priority from U.S. Provisional Patent Application No. 62/090,497 filed Dec. 11, 2014 and from U.S. Provisional Patent Application No. 62/132,597 filed Mar. 13, 2015, which are incorporated herein in their entirety.

TECHNICAL FIELD

The present invention relates to the field of automated external defibrillator storage devices.

BACKGROUND

Automated External Defibrillators (AEDs) are often used to resuscitate people during cardiac arrest incidents including life-threatening cardiac dysrhythmias, ventricular fibrillation, and pulseless ventricular tachycardia. Each of these cardiac incidents involves abnormal, electrical impulse conduction in the cardiac muscle, which in turn results in abnormal heart rhythms that may lead to damaged cardiac muscle and potentially death. To reduce the adverse effects and/or to end these incidents, defibrillation therapy, which includes delivering therapeutic doses of electrical current with a defibrillation device to the cardiac muscle thereby potentially restoring normal heart rhythm.

Numerous different types of defibrillator devices exist such as external, transvenous, or implanted defibrillator devices. For example, pacemakers are implantable devices used to treat people with chronic arrhythmias by constantly or intermittently applying compensatory and corrective electrical impulses to maintain proper cardiac rhythm. These compensatory and corrective electrical impulses thereby potentially reduce occurrence of cardiac arrest events and potentially prolong a person's life. While pacemakers are designed for patients having predictable, chronic cardiac arrhythmias, most cardiac arrests associated with life-threatening cardiac dysrhythmias, ventricular fibrillation, and pulseless ventricular tachycardia occur spontaneously. Therefore, specific AED devices were designed to further treat these spontaneous cardiac arrests.

Over the past four decades, it has become common place to include AED devices in various public and common areas having high volume pedestrian traffic to potentially combat the deleterious effects of the above mentioned spontaneous cardiac arrest incidents. Also, due to the complex and highly sensitive circuitry within these AED devices, these AED devices are sometimes placed within various types of storage cabinets to protect the AED devices until needed and to further ensure proper AED operation while in use. For example, U.S. Pat. No. 6,301,501 and U.S. Pat. No. 6,735,473 disclose exemplary, conventional AED storage cabinets. In order to notify others of someone potentially experiencing a cardiac arrest incident, most conventional cabinets are equipped with door triggered alarms that are activated and immediately sound (and/or provide a visual alarm) upon opening the cabinet door regardless of the presence of the AED device inside the cabinet.

Most conventional storage cabinets utilize an activation switch and alarm that is in operative relation relative to its door and a wall. More specifically, certain devices utilize a pressure switch operatively connected to a circuit that controls an alarm that is immediately activated upon door opening. In these exemplary devices, the pressure switch remains open as long as there is adequate pressure on the switch, which may be applied, for example, as long as the door is closed. However, when the storage cabinet door opens, pressure on the switch is released and the switch is closed, thus, automatically activating the alarm regardless of whether the AED device has been removed from the cabinet.

Although the above mentioned conventional AED storage cabinets function to store AED devices, many problems currently exist with these conventional cabinets. For example, cabinets having these "cover triggered" or "pressure triggered" alarms, which are operatively linked to door movement, are prone to generate false alarms. These false alarms may be generated when, for example, people accidentally bump into or make incidental contact with the storage device's door thereby partially or completely opening the door, which simultaneously activates the alarm. These false alarms create a general state of panic for those around the AED storage cabinet, and in some instances, medical providers (e.g., ambulances and emergency medical technicians) are unnecessarily alerted and called to the scene of the false alarm. Thus, these false alarms further waste healthcare provider's time and resources.

To potentially avoid these false alarms, many conventional AED storage cabinets have been further equipped with locking mechanisms (e.g., a lock and key mechanism) provided in the door that rely on keys for entry in to the cabinet's interior. However, a major drawback of including a lock and key mechanism in an AED storage cabinet is that the key must be readily accessible to unlock the door and access the AED device if someone is experiencing a cardiac arrest incident. Thus, even though a lock and key mechanism may decrease false alarms, these lock and key configurations often lead to decreased response times for treating cardiac arrest incidents.

SUMMARY

Therefore, a need exists to provide an AED storage cabinet that overcomes the deficiencies of conventional storage cabinets. Disclosed are automated defibrillator storage devices including a housing having walls and a door that define an interior cavity for receiving an automated defibrillator therein, a defibrillator stored within the storage cabinet, and an alarm positioned within the housing triggered in response to removal of the AED from the cabinet.

To achieve the foregoing, in a first embodiment the present invention provides a defibrillator storage device including a housing defining an interior storage compartment configured to hold a removable automated external defibrillator therein, a door pivotally attached along a bottom edge thereof to a bottom edge of the housing such that the door is configured to pivot open to access the interior storage compartment, an alarm disposed within the housing, and a tether attached at a first end thereof to an interior wall of the housing and at a second end thereof to the alarm, the tether configured to be routed through a handle of the automated external defibrillator such that removal of the automated external defibrillator from the interior compartment causes the second end of the tether to be pulled from the alarm, thereby triggering the alarm.

In another aspect, the alarm may be located on an interior wall of the housing opposite the interior wall to which the first end of the tether is attached, the alarm including a fixed plate and a body configured to translate relative to the fixed plate to move an electrical contact on the body relative to an electrical contact on the fixed plate, the electrical contact on the body and the electrical contact on the fixed plate together forming a switch for activating the alarm.

In another aspect, the second end of the tether may be threaded through an opening through the body and the body may include a resilient arm extending therefrom, the resilient arm engaging the interior wall to which the alarm is attached and arranged to bias the body in a direction of the fixed electrical contact when the tether is threaded through the opening through the body.

In another aspect, the opening through the body and the resilient arm may be arranged on opposite sides of the interior wall to which the alarm is attached such that threading of the second end of the tether through the opening of the body prevents the body from moving in a direction of the fixed electrical contact.

In another aspect, translation of the body relative to the fixed plate may be guided by a pair of spaced guides.

In another aspect, a heating device may be disposed within the housing in proximity of the automated external defibrillator to transfer radiant heat thereto.

In another aspect, a heating plate may be pivotally attached along a bottom edge thereof to the bottom edge of the housing inward of the door, the heating plate dimensioned to cover at least a portion of the automated external defibrillator to transfer radiant heat thereto.

In another aspect, a movable partition may be disposed within the housing defining a pocket for receiving the automated external defibrillator therein, the movable partition movable relative to a back wall of the housing and extending upward a predetermined distance from a floor of the housing.

In another aspect, the alarm may include an electrical circuit and a battery.

In another aspect, alarm activation may be independent of door movement.

In another embodiment, the present invention provides a defibrillator storage device including a housing defining an interior storage compartment configured to hold a removable automated external defibrillator therein, a door pivotally attached to the housing configured to pivot open to access the interior storage compartment, an alarm disposed within the housing external to the automated external defibrillator, and a tether attached at a first end thereof to an interior wall of the housing and at a second end thereof to the alarm, the tether configured to be routed through a handle of the automated external defibrillator such that removal of the automated external defibrillator from the interior compartment causes the second end of the tether to be pulled apart from the alarm, thereby triggering the alarm.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION

Figure 1:
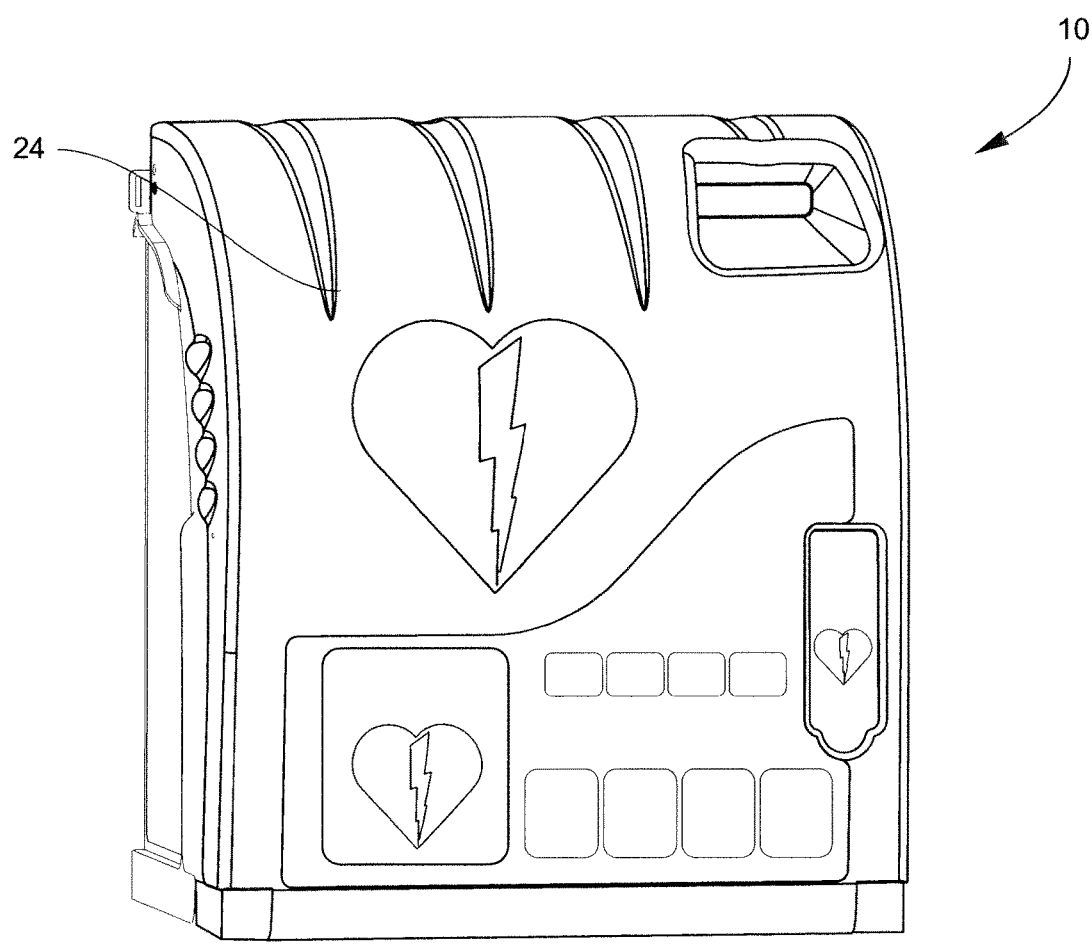
FIG. 1 is a perspective view of an Automated External Defibrillator (AED) storage device according to the present invention.
Figure 2A:
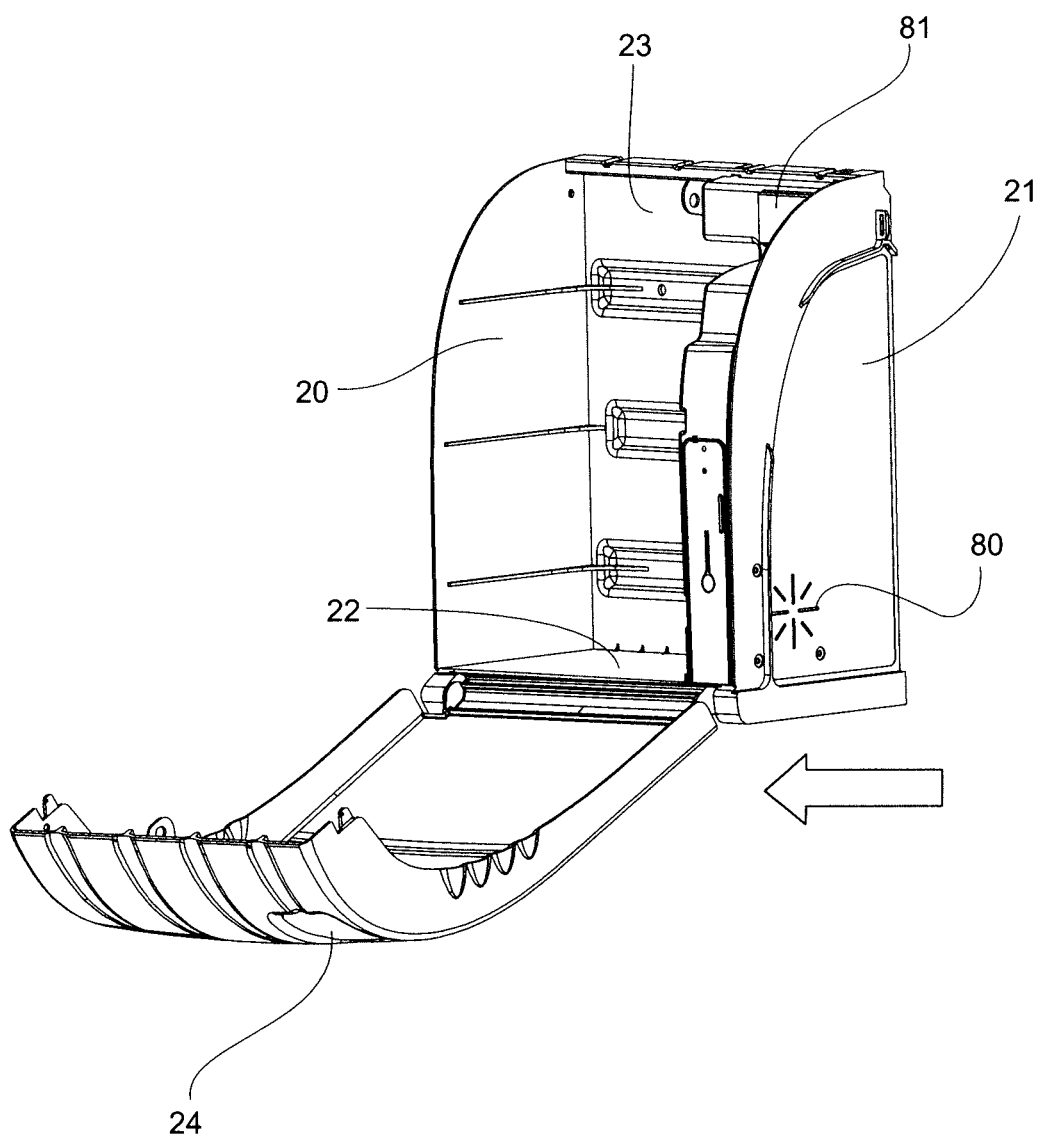
FIG. 2a is a perspective view of the AED storage device shown with the door opened and without an AED sored therein.
Figure 2B:
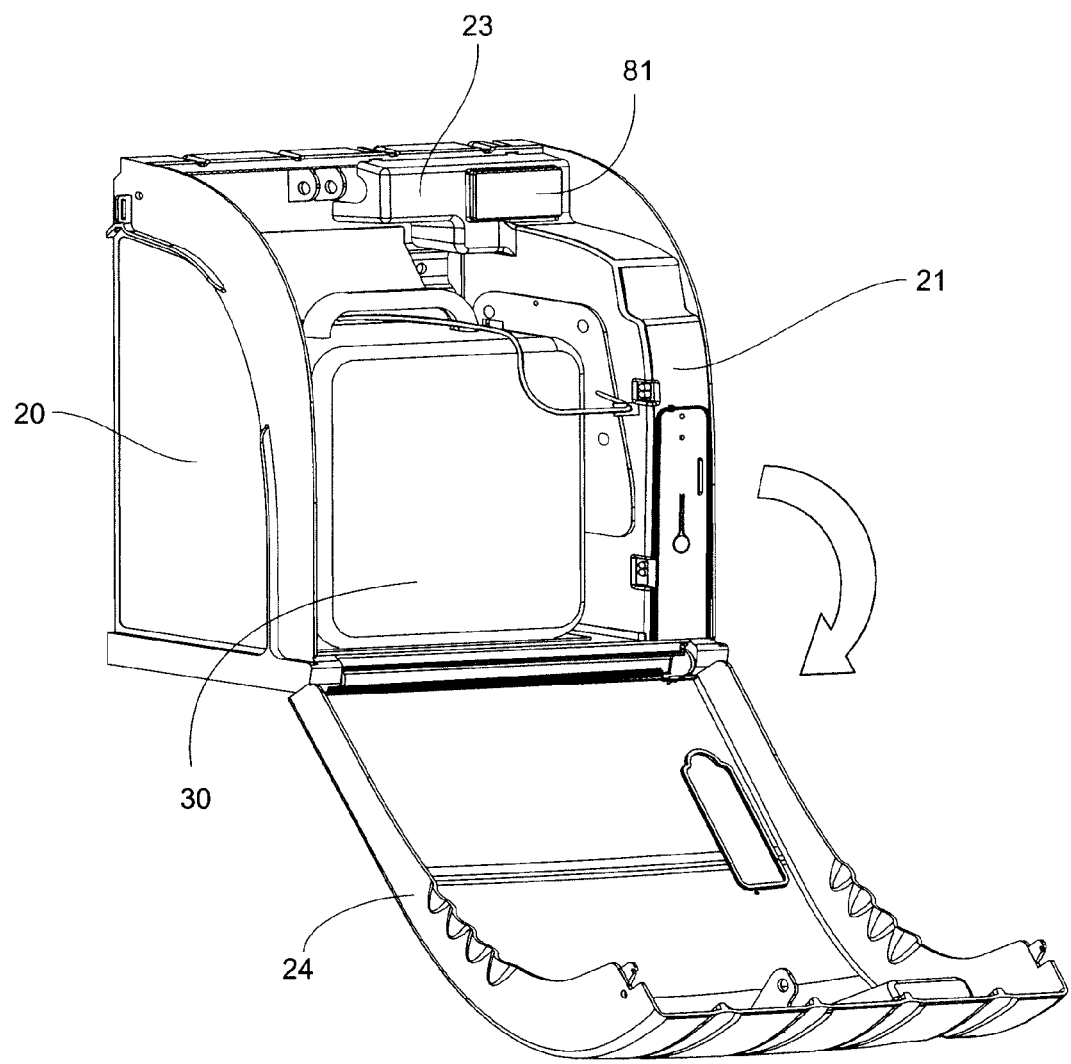
FIG. 2b depicts the AED storage device with the door opened and with an AED stored therein.

The present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

FIGS. 1-8 depict various views and embodiments of the AED storage device (also referred to as "the AED storage cabinet"). The disclosed automated defibrillator storage device 10, 110 (i.e., AED storage cabinet) includes a housing having walls 20, 21, 22, 23 and a door 24 that define an interior cavity for receiving an automated defibrillator 30. For example, storage device 10, 110 may include two side walls 20, 21 connected by a back wall 23, and bottom wall 22. Bottom wall 22 is connected to the side walls 20, 21 and back wall 23. When present, the AED device is preferably placed on the storage device's bottom wall 22, and is laterally adjacent to side walls 20, 21 and back wall 23.

In certain aspects, a lip is directly connected to and spans a partial or entire length of the bottom wall 22. The lip extends vertically from the bottom wall in a direction that is spaced apart and substantially parallel to the back wall 23. This lip has sufficient height (e.g., 1" to 6" in height, 2" to 5" in height, or 2.5" to 4" in height) to ensure that, when present, the AED device remains secured within cabinet 10, 110 upon opening door 24. In certain aspects, this lip, in combination with the side walls, back wall, and bottom wall, may form a recessed cavity within the interior of the storage device in which a bottom portion of the AED device may be obstructed from view when the AED device is placed within storage cabinet 10, 110. The walls 20, 21, 22, 23, door 24, and lip may be independently formed of rigid materials including thermoplastic resins (e.g., injection molded thermoplastic resin), metal, glass, or any combination thereof. In certain aspects, door 24 is preferably formed of a partially transparent thermoplastic resin such that the storage device's interior cavity, and more preferably the AED device, may be viewed when the door 24 is closed and the device is viewed from the outside.

In certain aspects, door 24 may be connected to an outer peripheral edge of the bottom wall 22 and pivot out and downward relative to a surface beneath device 10, 110 when opening the storage device. However, in alterative aspects, the door may be connected to a top portion (e.g., an outer peripheral edge) of the back wall 23 and may rotate in an upward manner relative to a surface beneath device 10, 110. The door may be further equipped with a locking mechanism to hold open the door if desired.

Figure 3:
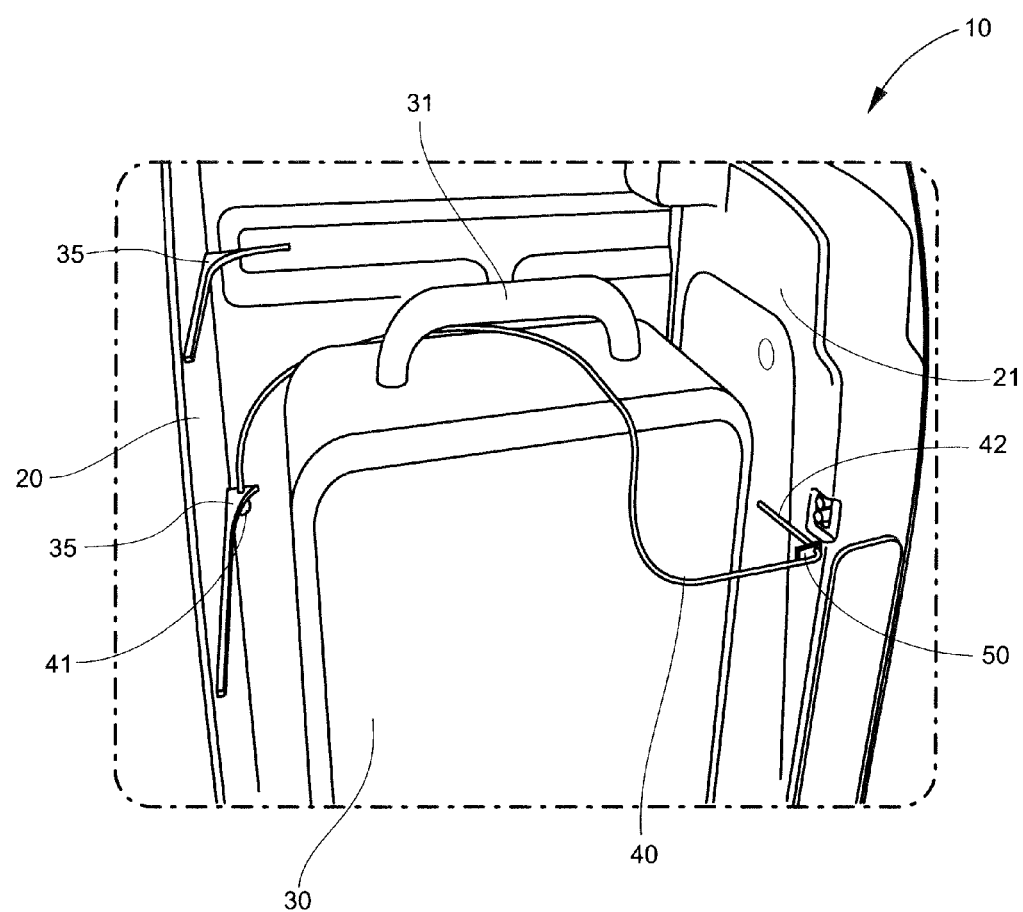
FIG. 3 is a detailed view of FIG. 2b further illustrating an AED in the storage device.
Figure 4:
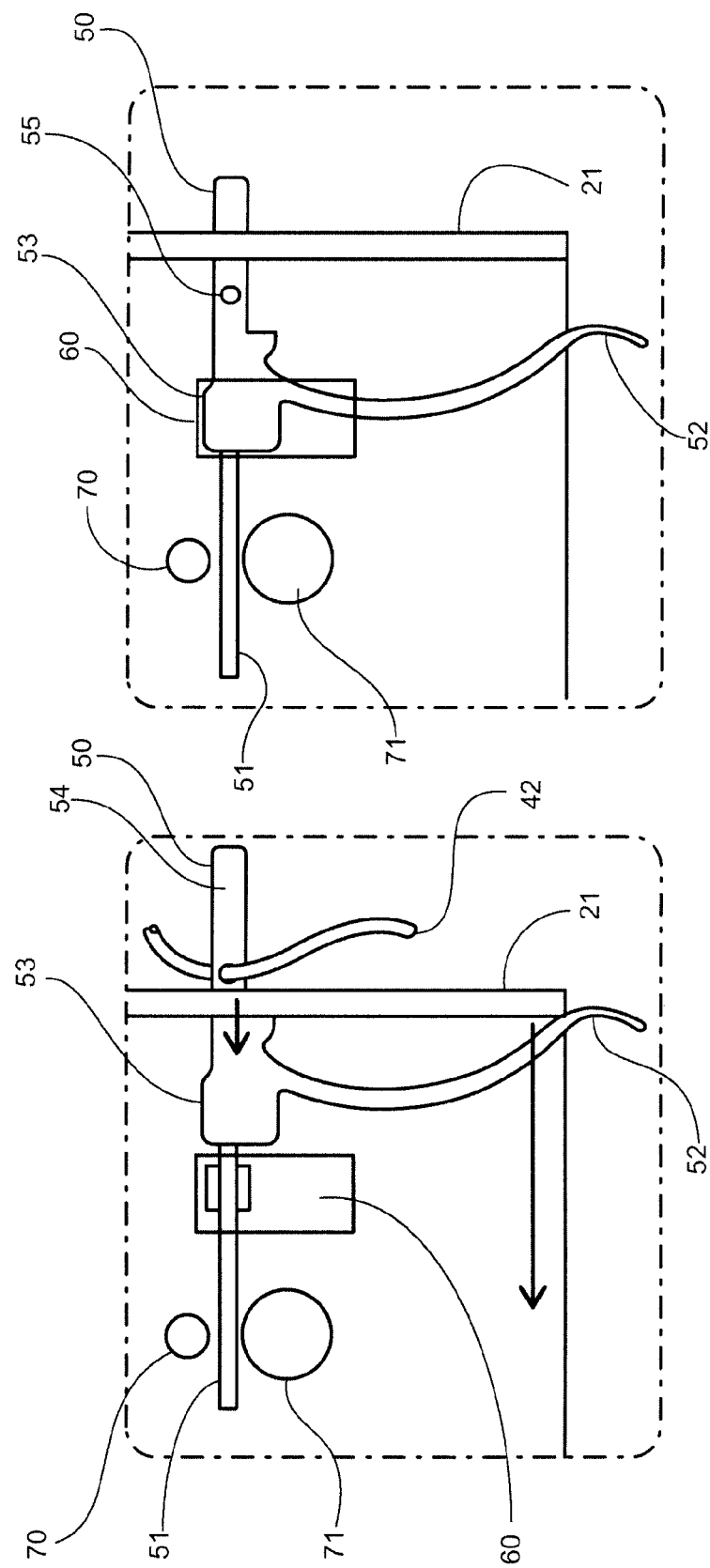
FIG. 4a and FIG. 4b are detailed, cut away views of the device sidewall illustrating movement of the activation switch/activation switch assembly to activate and deactivate the alarm according to one embodiment of the invention.
Figure 5:
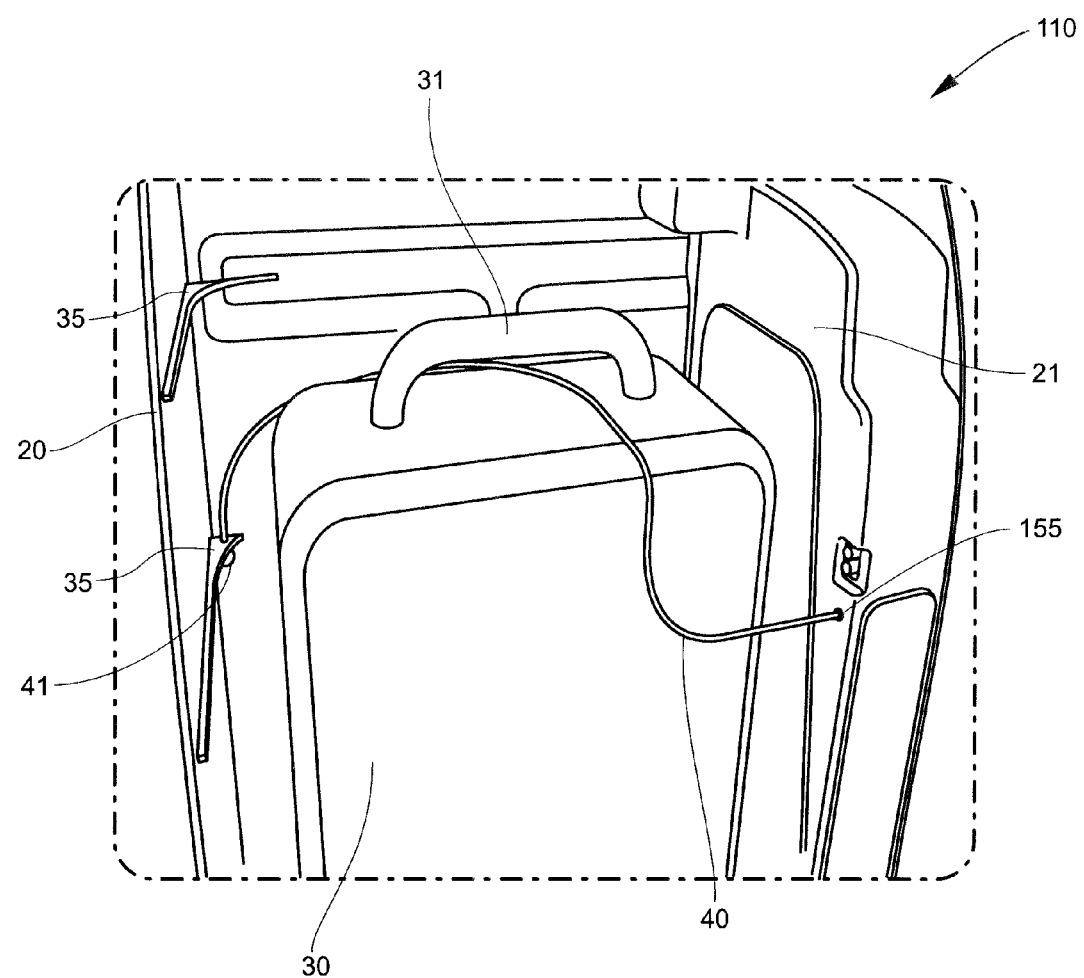
FIG. 5 is a detailed view of an AED inside the storage device with the alarm being activated but not actively alarming.

As depicted in FIGS. 3 and 5, storage device 10, 110 each include an alarm positioned within, for example, side wall 21. In certain aspects, the alarm may be mounted internally relative to wall 21 of the storage cabinet and external to defibrillator 30 The alarm includes a fixed plate 60 and a body 50 configured to translate relative to the fixed plate to move an electrical contact (not shown) on the body relative to an electrical contact on the fixed plate, the electrical contact on the body and the electrical contact on the fixed plate together forming a switch for activating the alarm.

Cable 40 having a first end 41 securely attached to or fixed to a rib 35 formed on the side wall 20 and back wall 23 of the cabinet interior. The cable 40 further includes a second end 42, 142 that is removably threaded through or removably tethered to an opening 55, 155. As shown in FIGS. 3 and 5, in certain aspects the cable is threaded through handle 31 of AED 30. In each aspect, when AED 30 is positioned within cabinet 10, 110 and cable 40 is tethered to the AED or threaded through handle 31, cable end 41 remains secured or fixed to rib 35 when AED 30 is removed from the cabinet. However, when AED 30 is removed from the cabinet, the second cable end 42, 142 is removed from opening 55, 155, thus activating the alarm.

In view of the above, the alarm depicted in FIGS. 3, 4a, and 4b will now be described in further detail. As shown in FIGS. 4a and 4b, in certain aspects, the body 50 has a "T" shape. With regard to this T shaped body, the T shaped body includes an elongate, rod-like structure with an end 54 arranged to protrude through side wall 21 and positioned externally relative to the side wall 21. The T shaped body includes an end 51 that is positioned within a mount 70, 71 (i.e., guides) such that the activation switch is movably attached in the cabinet 10 between side wall 21 and mount 70, 71 (i.e., guides). In certain aspects, ends 54, 51 are perpendicular relative a vertically extending face of wall 21. The T shaped body further includes arm 52 that extends co-axially relative to the vertical face of side wall 21, and a portion of arm 52 is configured to contact the inner portion of side wall 21. Arm 52 is preferably a resilient, elastic member configured to apply tensioned or compressive force against the inner portion of side wall 21 when the cable's second end 42 is placed in opening 55 and arm 52 moves the T shaped body when cable end 42 is removed, thus activating the alarm.

More particularly, FIG. 4a in view of FIG. 3 shows cable end 42 being inserted through an opening located on end 54 of the T shaped body, as well as arm 52 contacting side wall 21. The arrows in FIG. 4a indicate that arm 52 is elastically compressed against an inner portion of side wall 21 when cable end 42 is inserted in the T shaped body and is biased such that elastic force is simultaneously linearly exerted to provide translational movement from end 54 of the T shaped body to end 51 of the T shaped activation switch in a direction that is opposite from which cable end 42 is inserted. Also, FIG. 4a further depicts fixed plate 60 that is, for example, an electronic contactor that is operatively linked to the alarm and functions to activate the alarm when contacted by portion 53 of the body. However, as shown in FIG. 4a, cable end 42 prevents arm 52 from exerting elastic force such that portion 53 of the activation switch contacts the electronic contactor. Thus, when inserted, cable end 42 prevents the activation switch from contacting and activating the alarm (i.e., providing any visual and/or audible alarm signals 80).

As shown in FIG. 4b, when AED 30 is removed from cabinet 10, cable end 42 is removed from the opening located on end 50 of the body, and the body moves toward the electronic contactor (fixed plate 60) due to the elastic force exerted by arm 52 against the vertical face of the inner portion of side wall 21. In FIG. 4b, portion 53 of the body contacts the electronic contactor, thereby activating the alarm (e.g., an audible alarm 80, visual alarm 81, or a combination thereof). The alarm in cabinet 10 is preferably configured to remain activated until the activation switch is returned to the configuration shown in FIG. 4a. The alarm may be deactivated, for example, by pulling end 54 towards the interior of cabinet 10 and re-threading or re-tethering cable end 42 to the opening in end 54 of the activation switch. In certain aspects, the alarm may include a timer that deactivates the alarm after a predetermined time period lapses. For example, the alarm may include an audible alarm, a visual alarm (e.g., strobe lights), or a combination thereof that are programmed to alarm for a predetermined period of time (e.g., 1 minute, 5 minutes, etc.) once the AED device is removed from the storage device and may cease to alarm once the predetermined period of time has lapsed.

Figure 6A:
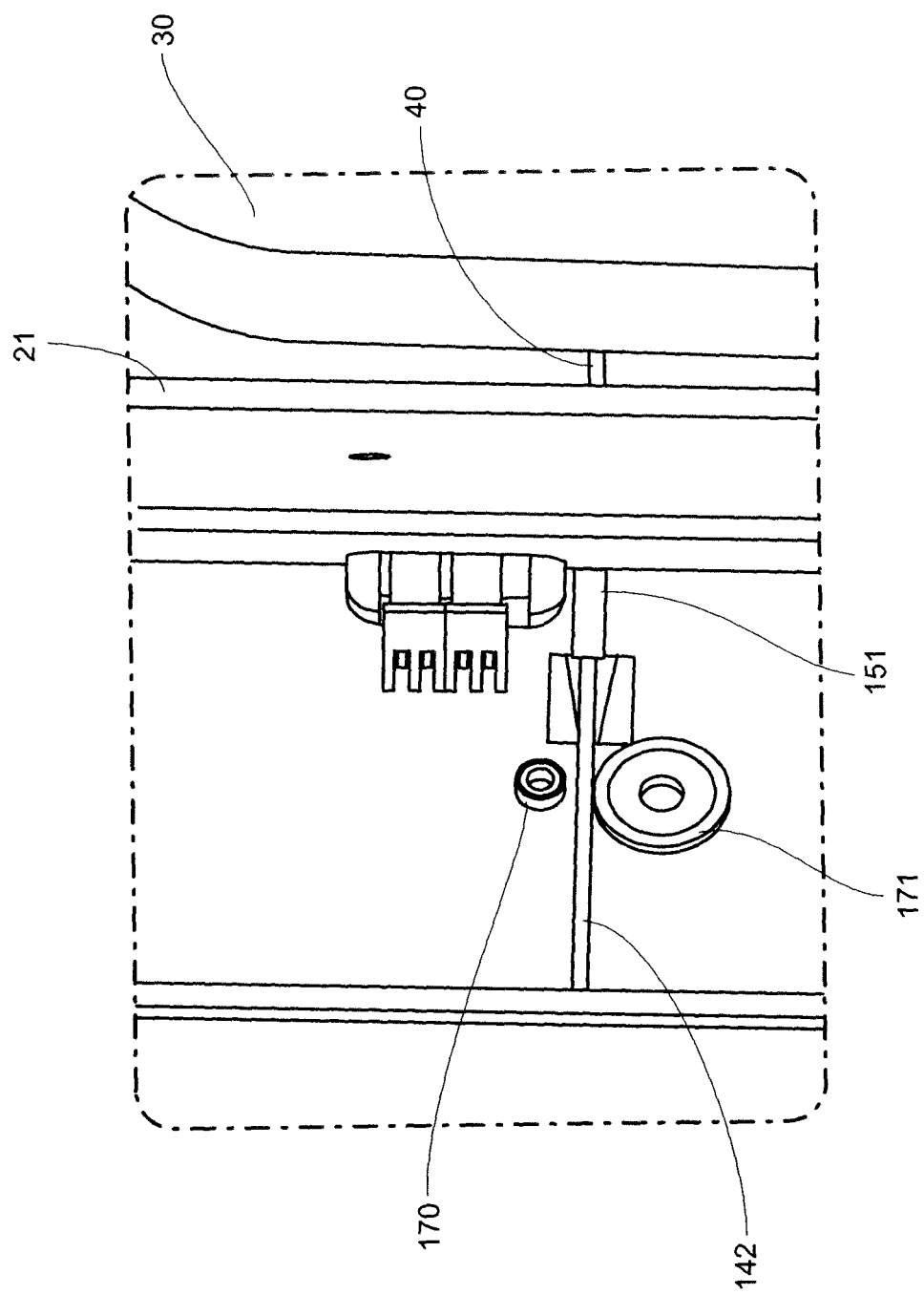
FIGS. 6(a) and 6(b) depict detailed cut-away views of the device's sidewall as depicted in the second embodiment.
Figure 6B:
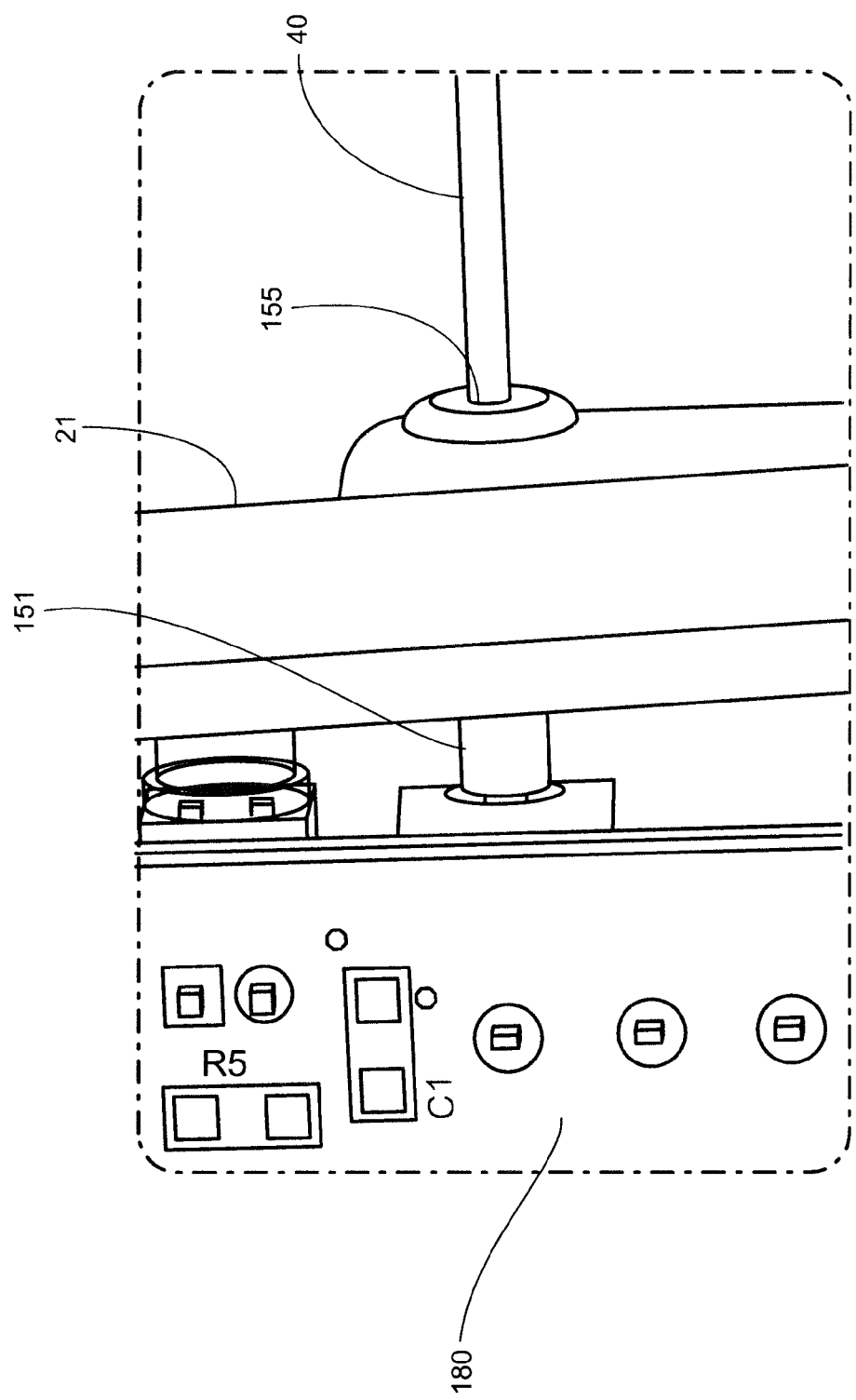
Figure 7A:
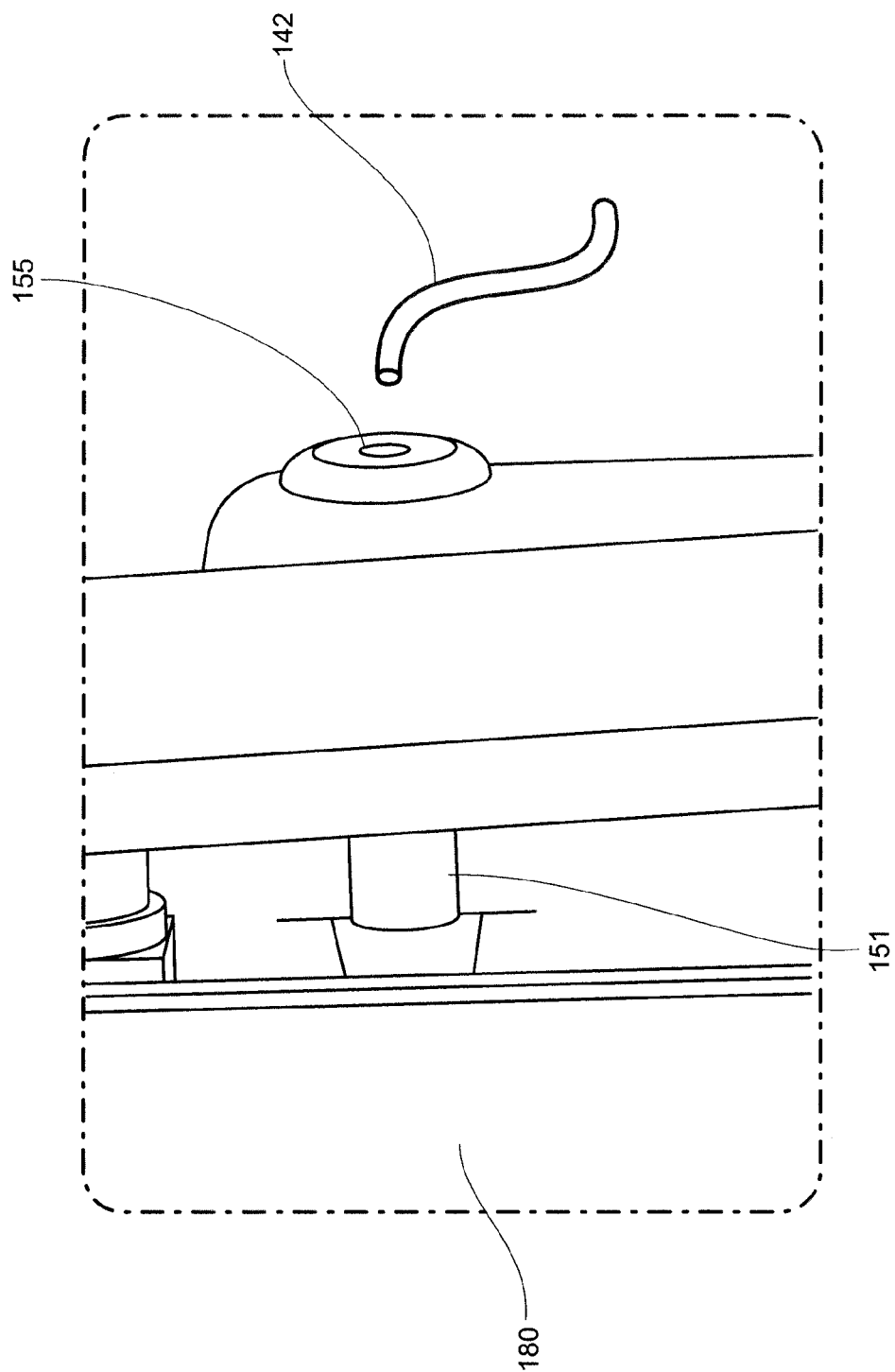
FIGS. 7(a), 7(b), 7(c), 8(a), and 8(b) depict various magnified, cut away cross section views of the device depicted in FIG. 5 illustrating alarm activation according to this embodiment of the invention.
Figure 7B:
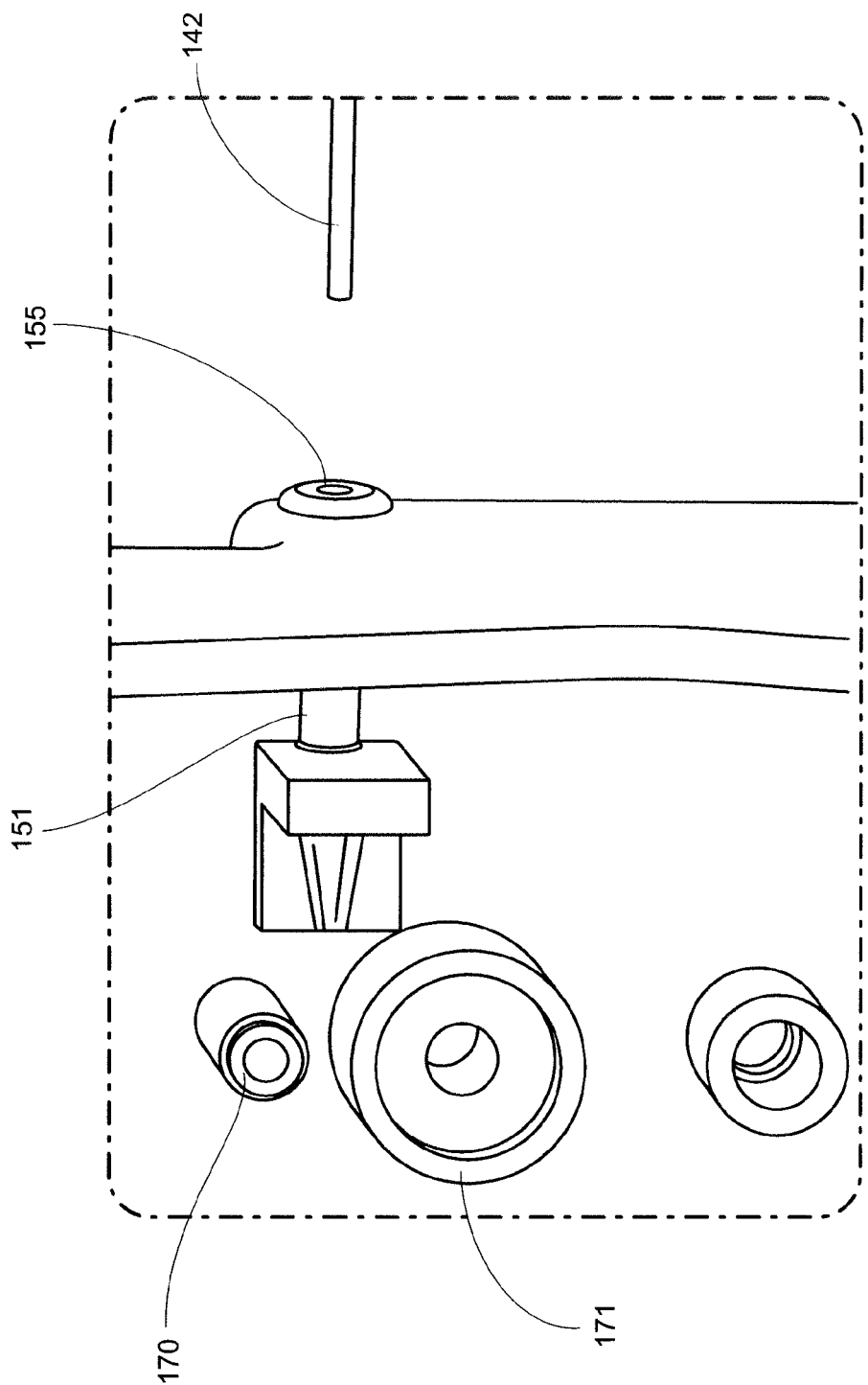
Figure 7C:
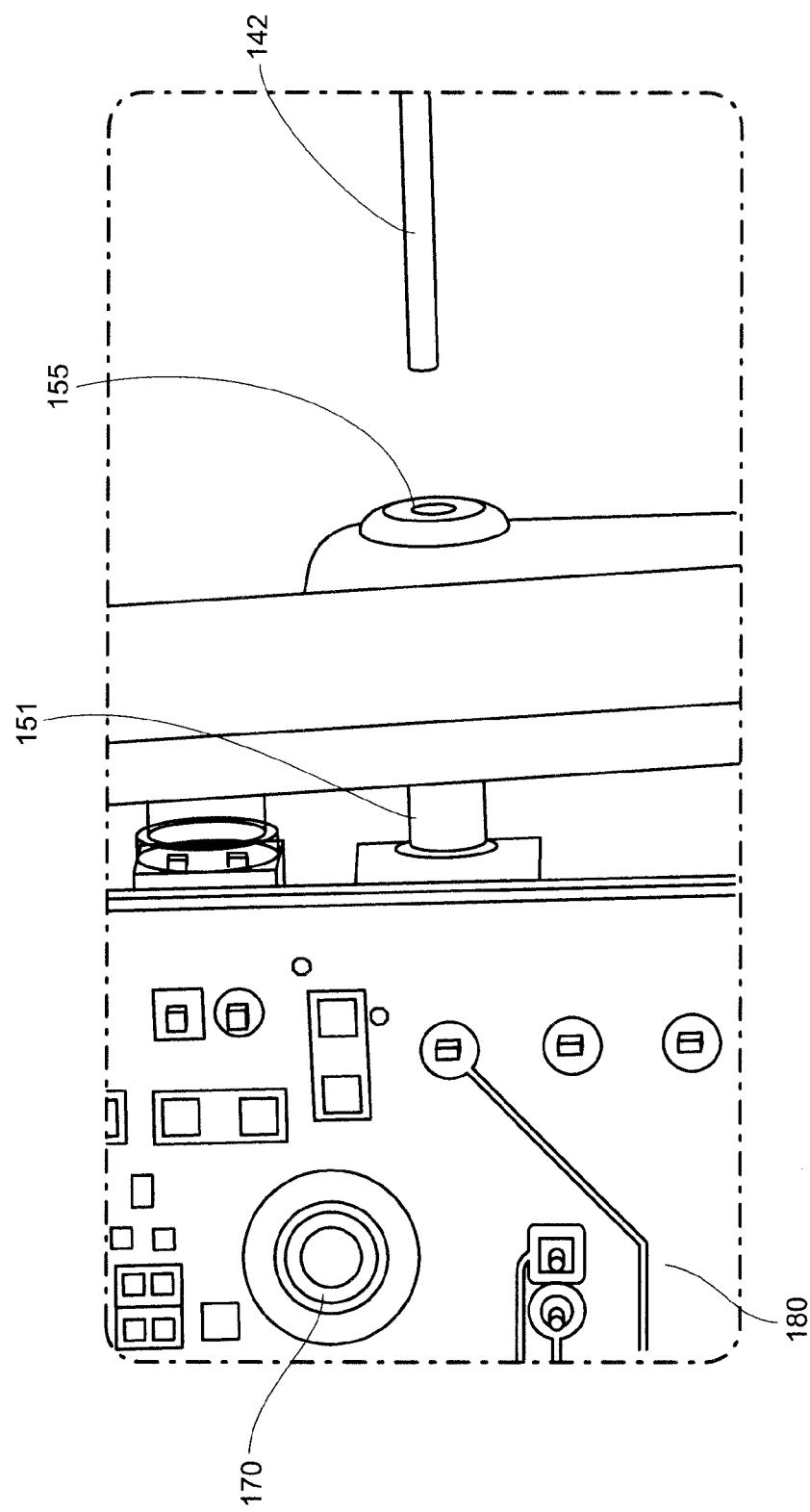
Figure 8A:
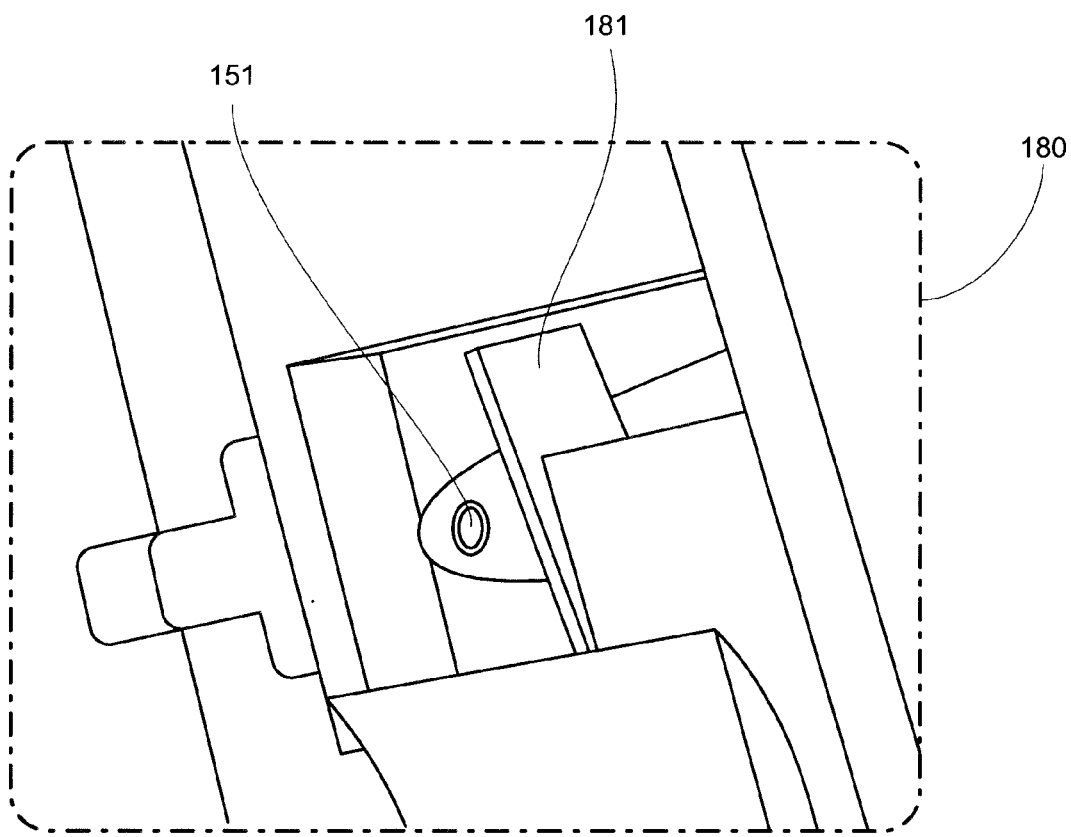
Figure 8B:
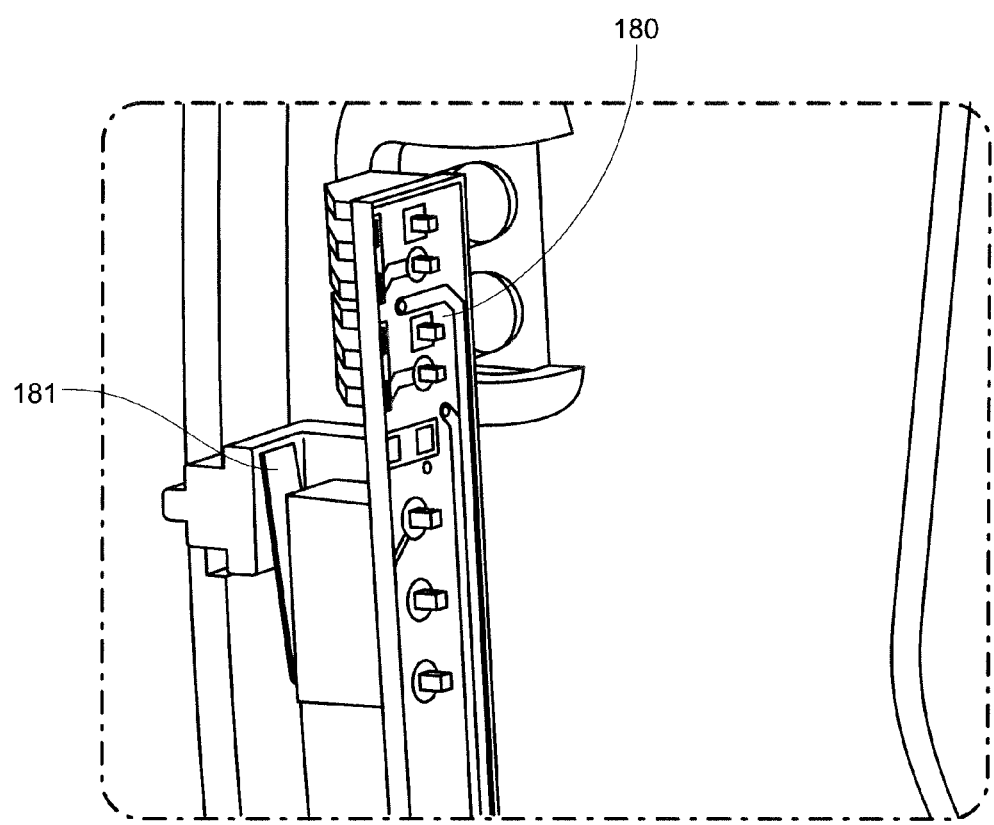

Another embodiment of the alarm will now be described in further detail in view of FIGS. 5-8(b). As shown in FIGS. 5, 6(a), and 6(b), opening 155 is provided on side wall 21 and cable end 142 is inserted into and threaded through this opening and preferably positioned between mounts 170, 171. When cable end 142 is inserted through opening 150 as depicted in FIG. 6, cable end 142 prevents a spring loaded electronic contactor 181 (FIGS. 8(a) and 8(b)) from being released and activating the alarm. However, as shown for example in FIG. 7(a)-FIG. 8(b), when cable end 142 is removed from opening 155, the spring loaded electronic contactor 181 is released thus activating the alarm. In particular, circuit 180 is operably connected to spring loaded electronic contactor 181, battery (not shown), and an audible and/or visual alarm. As indicated above, when removing AED 30 from the cabinet, cable end 142 is pulled from opening 155 allowing contactor 181 to close the circuit 180 thereby allowing current to flow from the battery through the circuit to the audible and/or visual alarm, thus activating the alarm and potentially notifying bystanders of a potential cardiac arrest incident. The alarm in cabinet 110 is preferably configured to remain activated until returning to the configuration shown in FIG. 6 by threading cable end 142 through opening 155 and disengaging the electronic contactor. In certain aspects, the alarm may include a timer that deactivates the alarm after a predetermined time period lapses.

Figure 9:
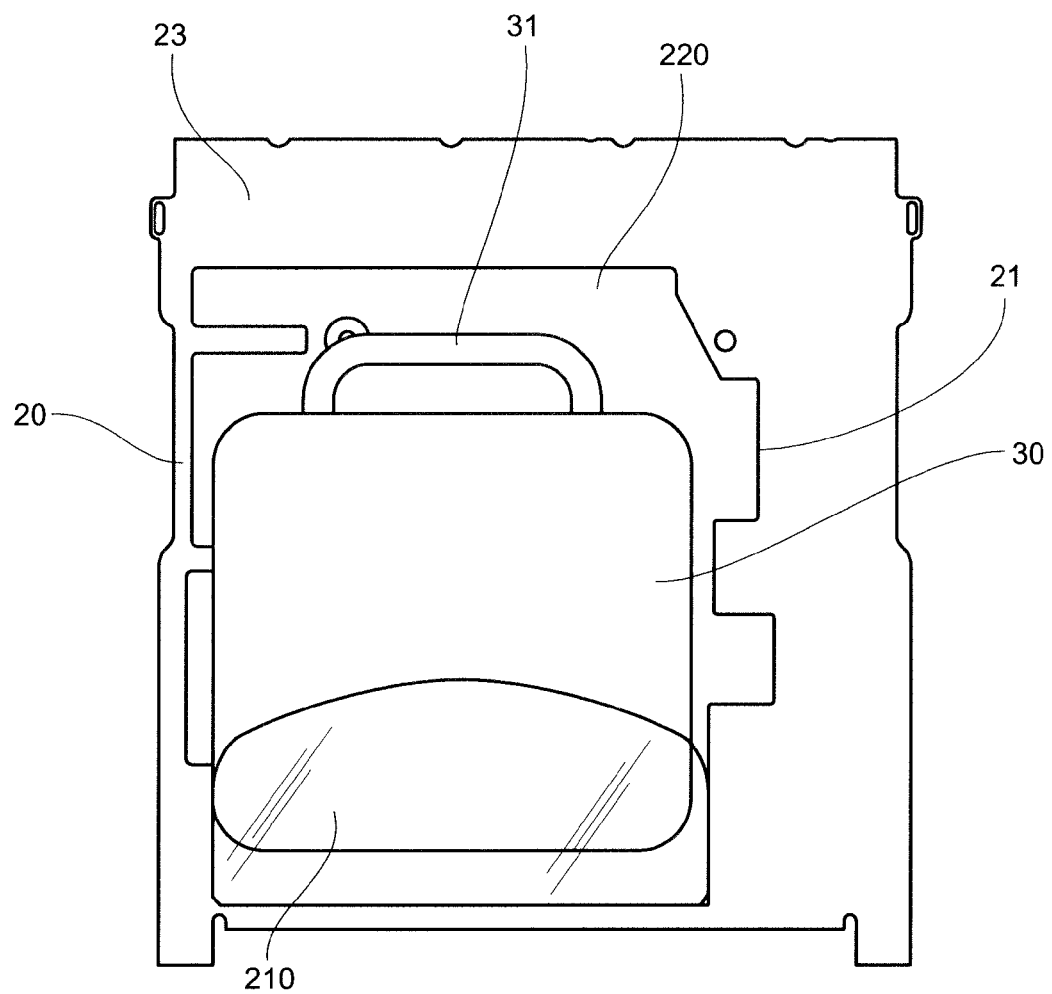
FIG. 9 is a front view of AED storage device with a securing element for securing the AED therein.
Figure 10A:
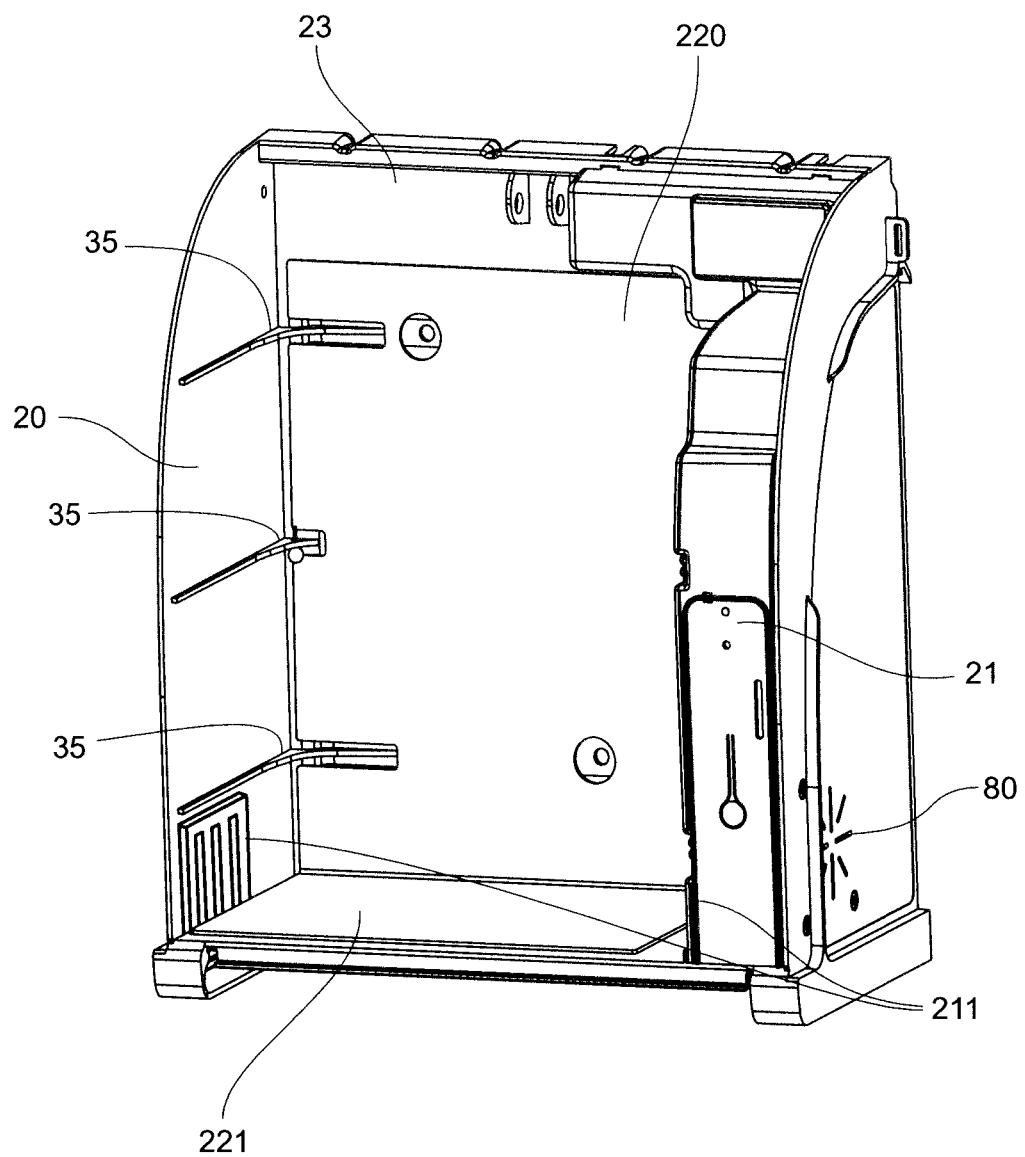
FIG. 10(a) depicts the AED device and securing element removed from the storage device.
Figure 10B:
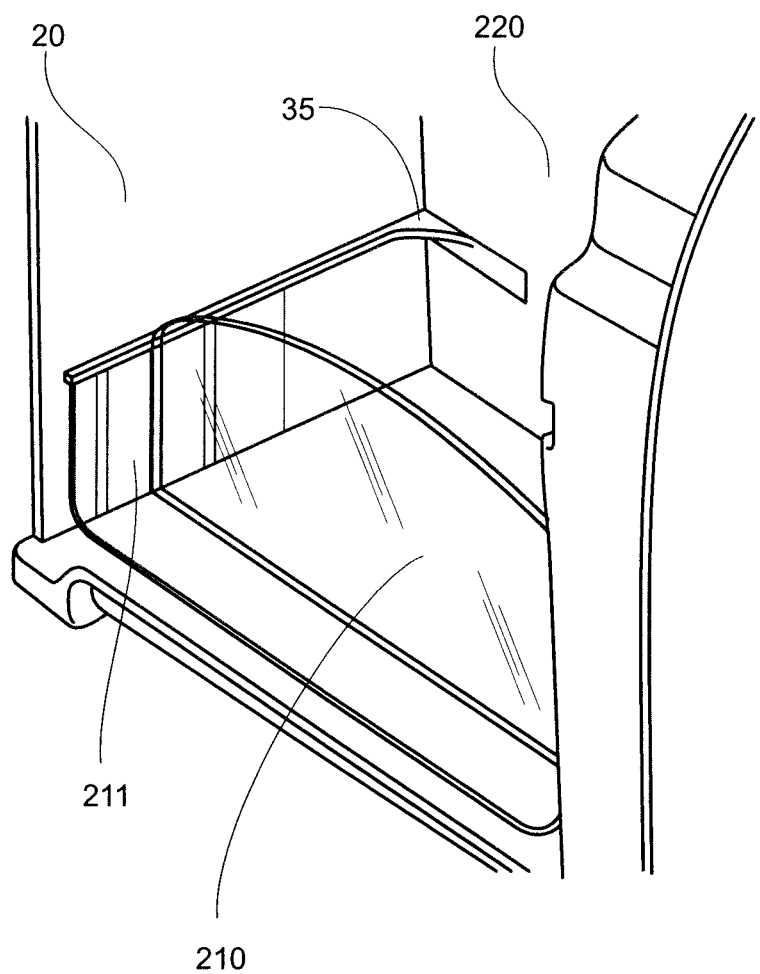
FIG. 10(b) depicts the AED device removed from storage device while the securing element remains positioned in the storage device.
Figure 11B:
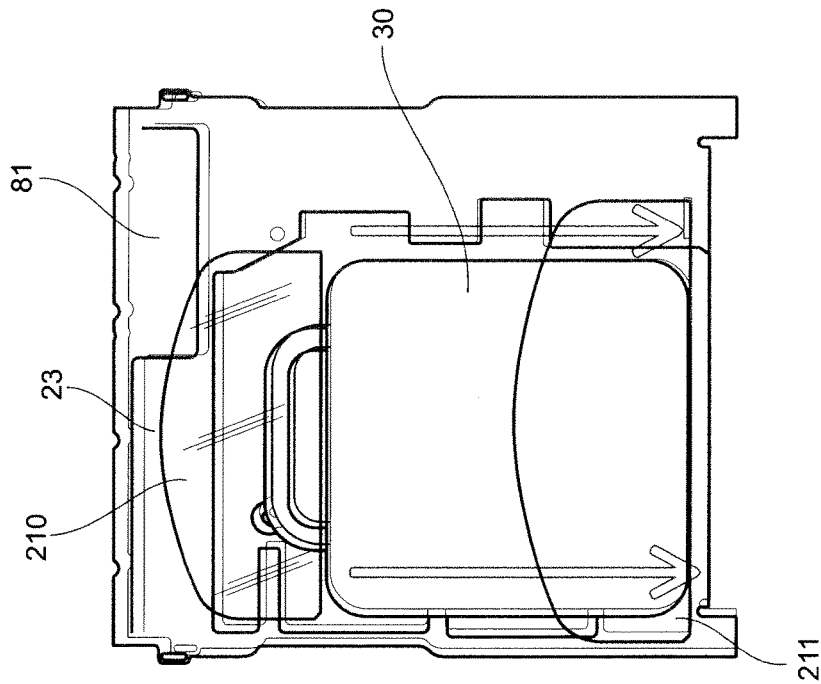
FIGS. 11(a), 11(b), and 11(c) sequentially depict securing element installation.
Figure 11A:
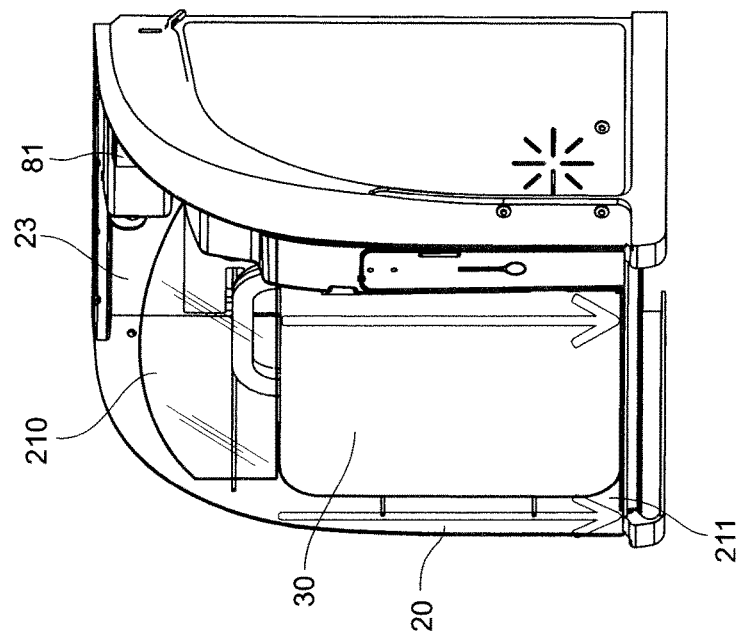
Figure 11C:
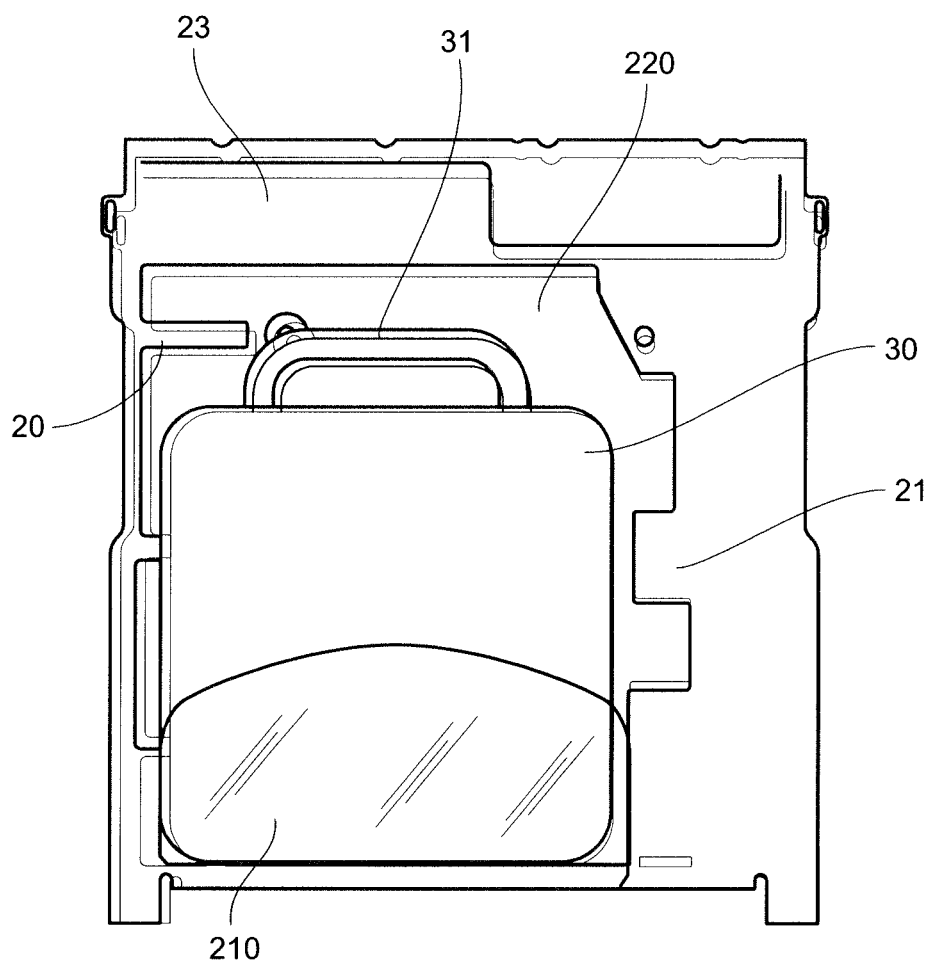

FIGS. 9-15 depict the storage devices 10, 110 disclosed herein being further equipped with heater 220, 221 and securing elements 210, 310 that respectively heat and securely position and hold AED 30 within the storage device(s). FIGS. 9-11(*c*) depict a storage device 10, 110 equipped with securing element 210 (i.e., partition) and heater 220, 221 according to one embodiment. As shown within FIGS. 10(*a*) and 10(*b*), storage device 10, 110 may include tracks 211 attached to an outer portion of opposing walls 20, 21. Tracks 211 preferably include one or a plurality of grooves that are aligned relative to the grooves on the track positioned on the opposing wall. These grooves are configured to receive securing element 210 (e.g., a flat, thin partition that may be translucent and/or transparent material such as a molded, thermoplastic, glass, or other composite material), which extends perpendicularly relative to an outer surface of bottom wall 22 when securing element 210 is positioned in tracks 211. The grooves further allow for securing element 210 to be positioned at various depths within the storage device's interior to secure different AEDs having variable widths.

FIGS. 11(*a*)-11(*c*) further sequentially depict securing element 210 (e.g., a flat, thin partition) being installed to secure an AED within the interior cavity of storage device 10, 110. For example, FIGS. 11(*a*) and 11(*b*) specifically depict securing element 210 being positioned within the interior cavity of storage device 10, 110 and being aligned with the grooves of securing element tracks 211. After aligning securing element 210 with grooves of tracks 211, securing element 210 is pressed in a downward manner such that securing element slidably engages the grooves thereby becoming fixed within the interior cavity of device 10, 110, and in certain aspects, securing element 210 contacts the outer surface of bottom wall 22 when fixed in tracks 211. The fixed securing element 210 extends upward from the cabinet floor (i.e., bottom wall 22) and has sufficient height relative to to AED 30 to secure the AED within the interior cavity. For example, in certain aspects, securing element 210 is configured to extend/have a height between approximately ¼ to ½ of the height of the AED; this height may include from 4 to 10 inches, from 5 to 9 inches, or from 6 to 8 inches when measured extending upward from bottom wall 22. As alluded to above, storage device 10, 110 further includes a heater 220, 221 positioned on inner circumferential portions of, for example, walls 22, 23 that define portions of the interior cavity. Heater 220, 221 is preferably configured to circumferentially surround portions of AED 30 and is configured to provide radiant heat to the AED during harsh, cold weather conditions to prevent and/or reduce the likelihood of AED malfunction associated with harsh weather conditions.

Figure 12:
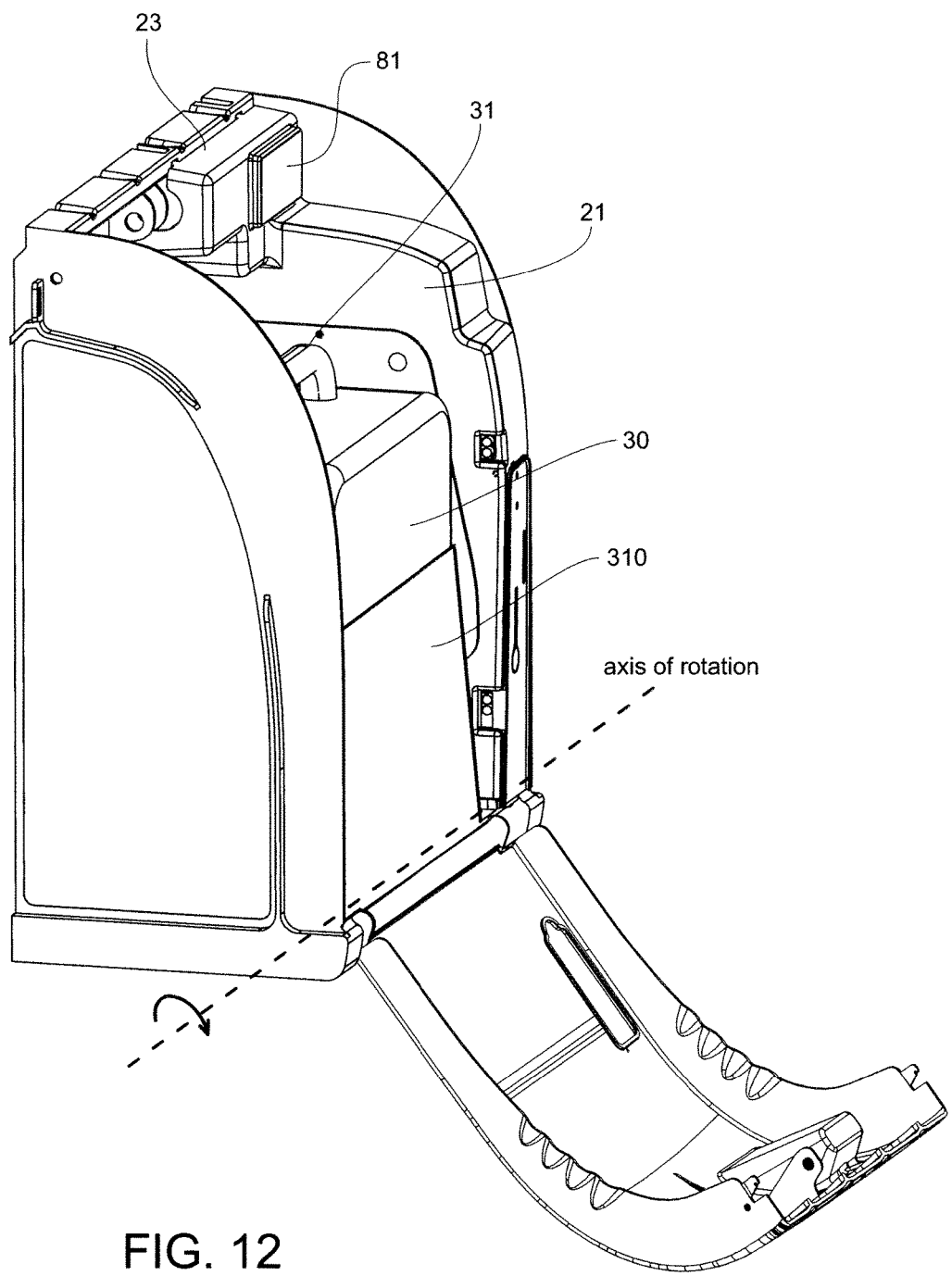
FIG. 12 depicts a second embodiment of the securing element for securing the AED within the storage device.
Figure 13:
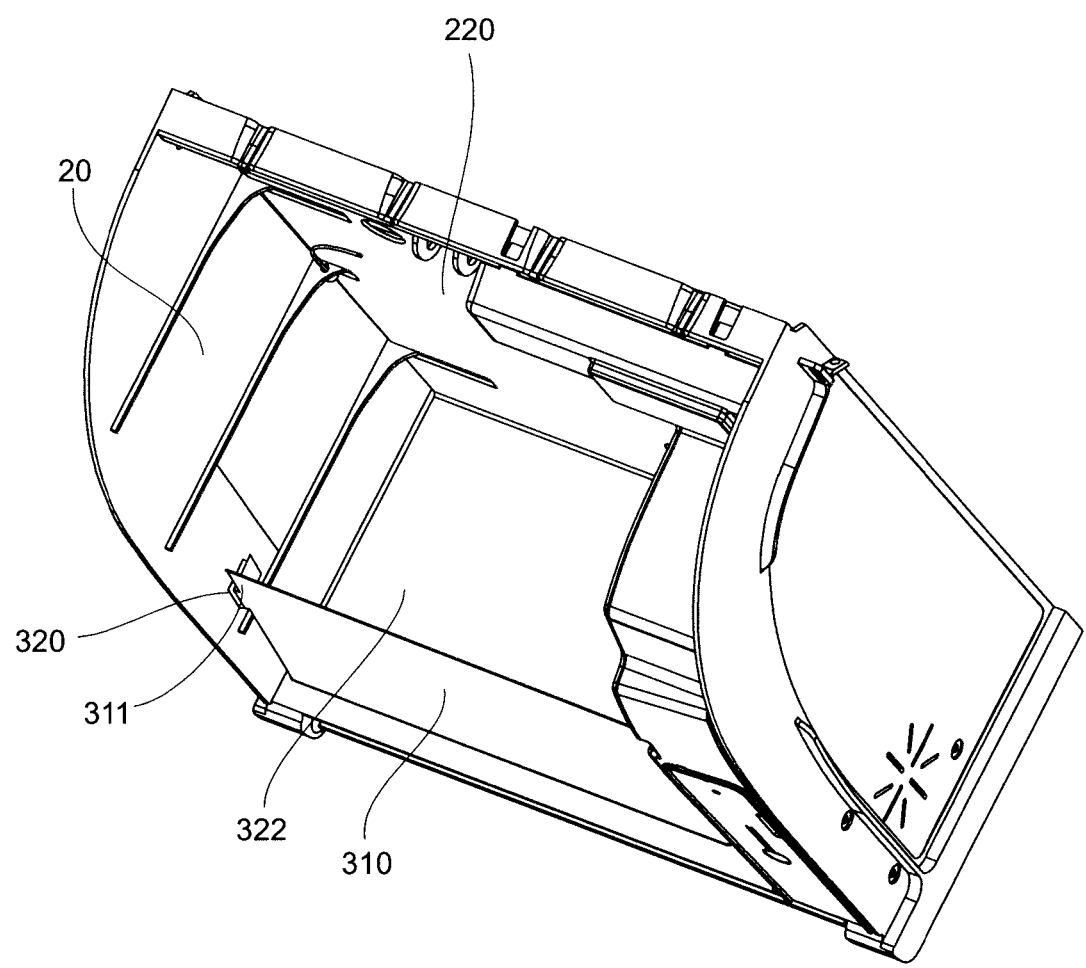
FIG. 13 is a top view depicting the second embodiment of the securing element shown with the AED removed from the device.
Figure 14:
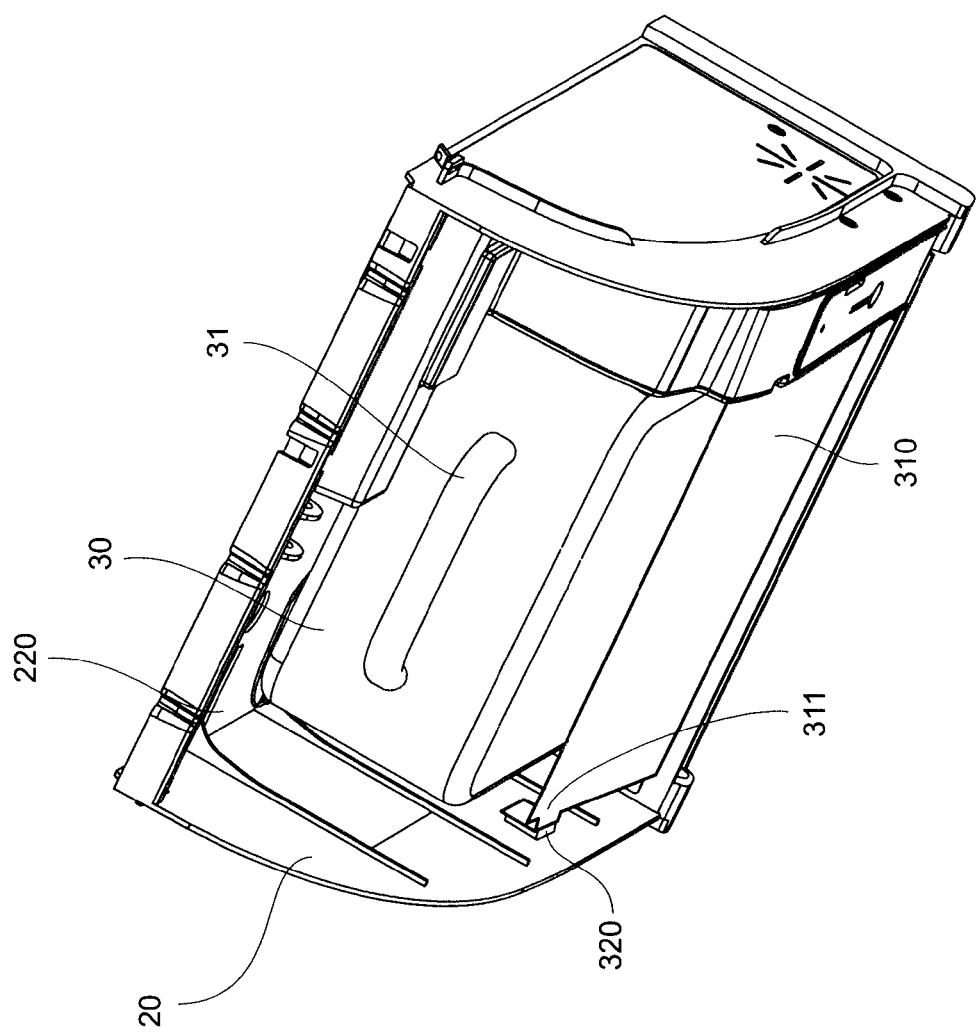
FIG. 14 is a top view depicting the second embodiment of the securing element with the AED positioned in the interior of the storage device.

FIGS. 12-15 depict a storage device 10, 110 equipped with securing element 310 (i.e., movable partition) configured to securely hold AED 30 within the interior cavity of the storage device according to a second embodiment. As depicted in FIG. 12, securing element 310 (i.e., movable partition) may be pivotably attached to bottom wall 22 and configured to pivot about a horizontal axis that is parallel to the horizontal axis of bottom wall 22. As further depicted in FIGS. 13-15, securing element 310 has complimentary detachable fasteners 320 positioned on walls 20, 21 and end portions 311 of the securing element. In certain aspects, end portions 311 may be tabs that are perpendicular relative to the main body of securing element 310 and extend into the interior cavity of storage device 10, 110 when securing element is in a closed, fastened position (i.e., a "securing" position). The complimentary detachable fasteners 320 may include, but are not limited to, complimentary hook and loop fasteners that may be detached from one another thereby allowing securing element 310 to detach from wall(s) 20, 21 to rotate away from the storage device's interior cavity (or AED 31 if present) into an opened, "non-securing" position.

Figure 15:
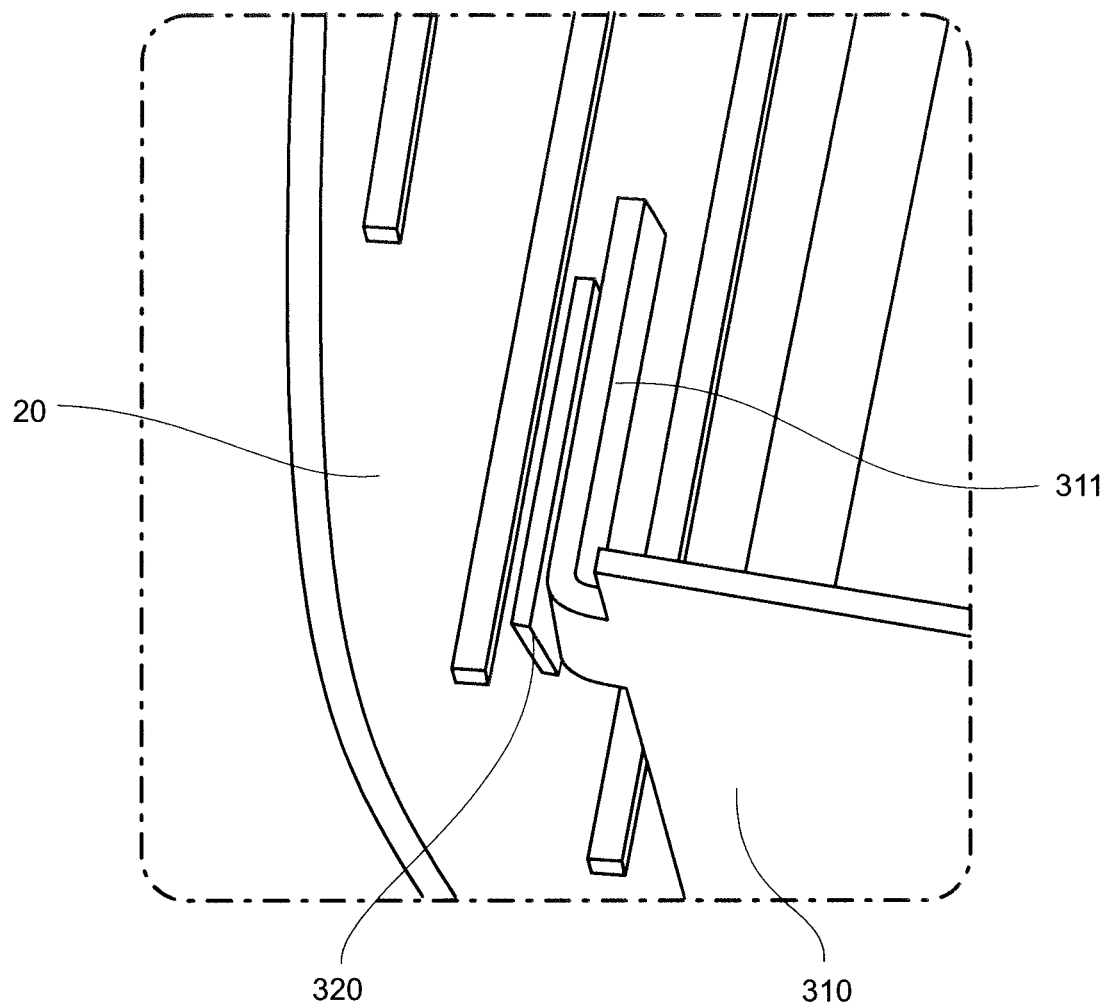
FIG. 15 is a detailed view of the exemplary fixing elements used to secure the second embodiment of the securing element in the interior of the storage device.

In certain aspects, securing element 310 further includes fastener 322 positioned mid-span along a top edge of the securing element 310. Fastener 322 may include a hook or loop fastener, and AED 30 may have a complimentary hook or loop fastener positioned accordingly such that fastener 322 contacts the complimentary hook or loop fastener on the AED 30 thereby further aiding in securing the AED within the interior portion of the device 10, 110. FIG. 15 provides a magnified view of the detachable fastener 320 used to secure the securing feature 310 in the interior of the storage cabinet. As alluded to above, storage device 10, 110 depicted in FIGS. 12-15 further includes a heater 220, 221 positioned on inner circumferential portions of, for example, walls 22, 23 that define portions of the interior cavity. Heater 220, 221 circumferentially surrounds portions of AED 30 and is configured to heat the AED during harsh, cold weather conditions to reduce the likelihood of AED malfunction associated with harsh weather conditions.

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. A defibrillator storage device, comprising:
   a housing defining an interior storage compartment configured to hold a removable automated external defibrillator therein;
   a door pivotally attached along a bottom edge thereof to a bottom edge of the housing such that the door is configured to pivot open to access the interior storage compartment;
   an alarm disposed within the housing;
   a tether attached at a first end thereof to an interior wall of the housing and at a second end thereof to the alarm, the tether configured to be routed through a handle of the automated external defibrillator such that removal of the automated external defibrillator from the interior compartment causes the second end of the tether to be pulled from the alarm, thereby triggering the alarm; and
   a heating plate pivotally attached along a bottom edge thereof to the bottom edge of the housing inward of the door, the heating plate dimensioned to cover at least a portion of the automated external defibrillator to transfer radiant heat thereto.

2. The defibrillator storage device of claim 1, wherein the alarm is located on an interior wall of the housing opposite the interior wall to which the first end of the tether is attached, the alarm comprising a fixed plate and a body configured to translate relative to the fixed plate to move an electrical contact on the body relative to an electrical contact on the fixed plate, the electrical contact on the body and the electrical contact on the fixed plate together forming a switch for activating the alarm.

3. The defibrillator storage device of claim 2, wherein the second end of the tether is threaded through an opening through the body and the body comprises a resilient arm extending therefrom, the resilient arm engaging the interior wall to which the alarm is attached and arranged to bias the body in a direction of the fixed electrical contact when the tether is threaded through the opening through the body.

4. The defibrillator storage device of claim 3, wherein the opening through the body and the resilient arm are arranged on opposite sides of the interior wall to which the alarm is attached such that threading of the second end of the tether through the opening of the body prevents the body from moving in a direction of the fixed electrical contact.

5. The defibrillator storage device of claim 3, wherein translation of the body relative to the fixed plate is guided by a pair of spaced guides.

6. The defibrillator device of claim 1, further comprising a heating device disposed within the housing in proximity of the automated external defibrillator to transfer radiant heat thereto.

7. The defibrillator device of claim 1, further comprising a movable partition disposed within the housing defining a pocket for receiving the automated external defibrillator therein, the movable partition movable relative to a back wall of the housing and extending upward a predetermined distance from a floor of the housing.

8. The defibrillator device of claim 1, wherein the alarm comprises an electrical circuit and a battery.

9. The defibrillator device of claim 1, wherein alarm activation is independent of door movement.

10. A defibrillator storage device, comprising:
a housing defining an interior storage compartment configured to hold a removable automated external defibrillator therein;
a door pivotally attached to the housing, the door configured to pivot open to access the interior storage compartment;
an alarm disposed within the housing external to the automated external defibrillator;
a tether attached at a first end thereof to an interior wall of the housing and at a second end thereof to the alarm, the tether configured to be routed through a handle of the automated external defibrillator such that removal of the automated external defibrillator from the interior compartment causes the second end of the tether to be pulled apart from the alarm, thereby triggering the alarm; and
a heating plate dimensioned to cover at least a portion of the automated external defibrillator to transfer radiant heat thereto.

11. The defibrillator storage device of claim 10, wherein the alarm is located on an interior wall of the housing, the alarm comprising a fixed plate and a body configured to translate relative to the fixed plate to move an electrical contact on the body relative to an electrical contact on the fixed plate, the electrical contact on the body and the electrical contact on the fixed plate together forming a switch for activating the alarm.

12. The defibrillator storage device of claim 11, wherein the second end of the tether is threaded through an opening through the body and the body comprises a resilient arm extending therefrom, the resilient arm engaging the interior wall to which the alarm is attached and arranged to bias the body in a direction of the fixed electrical contact when the tether is threaded through the opening through the body.

13. The defibrillator storage device of claim 12, wherein the opening through the body and the resilient arm are arranged on opposite sides of the interior wall to which the alarm is attached such that threading of the second end of the tether through the opening of the body prevents the body from moving in a direction of the fixed electrical contact.

14. The defibrillator storage device of claim 12, wherein translation of the body relative to the fixed plate is guided by a pair of spaced guides.

15. The defibrillator device of claim 10, further comprising a heating device disposed within the housing in proximity of the automated external defibrillator to transfer radiant heat thereto.

16. The defibrillator device of claim 10, further comprising a movable partition disposed within the housing defining a pocket for receiving the automated external defibrillator therein, the movable partition movable relative to a back wall of the housing and extending upward a predetermined distance from a floor of the housing.

17. The defibrillator device of claim 10, wherein the alarm comprises an electrical circuit and a battery.

18. The defibrillator device of claim 10, wherein alarm activation is independent of door movement.

19. A defibrillator storage device, comprising:
a housing defining an interior storage compartment configured to hold a removable automated external defibrillator therein;
a door pivotally attached along a bottom edge thereof to a bottom edge of the housing such that the door is configured to pivot open to access the interior storage compartment;
an alarm disposed within the housing; and
a tether attached at a first end thereof to an interior wall of the housing and at a second end thereof to the alarm, the tether configured to be routed through a handle of the automated external defibrillator such that removal of the automated external defibrillator from the interior compartment causes the second end of the tether to be pulled from the alarm, thereby triggering the alarm, wherein:
the alarm is located on an interior wall of the housing opposite the interior wall to which the first end of the tether is attached, the alarm comprising a fixed plate and a body configured to translate relative to the fixed plate to move an electrical contact on the body relative to an electrical contact on the fixed plate, the electrical contact on the body and the electrical contact on the fixed plate together forming a switch for activating the alarm and
the second end of the tether is threaded through an opening through the body and the body comprises a resilient arm extending therefrom, the resilient arm engaging the interior wall to which the alarm is attached and arranged to bias the body in a direction of the fixed electrical contact when the tether is threaded through the opening through the body.

20. The defibrillator storage device of claim 19, wherein the opening through the body and the resilient arm are arranged on opposite sides of the interior wall to which the alarm is attached such that threading of the second end of the tether through the opening of the body prevents the body from moving in a direction of the fixed electrical contact.

21. The defibrillator storage device of claim 19, wherein translation of the body relative to the fixed plate is guided by a pair of spaced guides.

22. The defibrillator device of claim 19, further comprising a heating device disposed within the housing in proximity of the automated external defibrillator to transfer radiant heat thereto.

23. The defibrillator device of claim 19, further comprising a heating plate pivotally attached along a bottom edge thereof to the bottom edge of the housing inward of the door, the heating plate dimensioned to cover at least a portion of the automated external defibrillator to transfer radiant heat thereto.

24. The defibrillator device of claim 19, further comprising a movable partition disposed within the housing defining a pocket for receiving the automated external defibrillator therein, the movable partition movable relative to a back wall of the housing and extending upward a predetermined distance from a floor of the housing.

25. The defibrillator device of claim 19, wherein the alarm comprises an electrical circuit and a battery.

26. The defibrillator device of claim 19, wherein alarm activation is independent of door movement.

27. A defibrillator storage device, comprising:
a housing defining an interior storage compartment configured to hold a removable automated external defibrillator therein;
a door pivotally attached to the housing, the door configured to pivot open to access the interior storage compartment;
an alarm disposed within the housing external to the automated external defibrillator; and
a tether attached at a first end thereof to an interior wall of the housing and at a second end thereof to the alarm, the tether configured to be routed through a handle of the automated external defibrillator such that removal of the automated external defibrillator from the interior compartment causes the second end of the tether to be pulled apart from the alarm, thereby triggering the alarm, wherein:
the alarm is located on an interior wall of the housing, the alarm comprising a fixed plate and a body configured to translate relative to the fixed plate to move an electrical contact on the body relative to an electrical contact on the fixed plate, the electrical contact on the body and the electrical contact on the fixed plate together forming a switch for activating the alarm, and
the second end of the tether is threaded through an opening through the body and the body comprises a resilient arm extending therefrom, the resilient arm engaging the interior wall to which the alarm is attached and arranged to bias the body in a direction of the fixed electrical contact when the tether is threaded through the opening through the body.

28. The defibrillator storage device of claim 27, wherein the opening through the body and the resilient arm are arranged on opposite sides of the interior wall to which the alarm is attached such that threading of the second end of the tether through the opening of the body prevents the body from moving in a direction of the fixed electrical contact.

29. The defibrillator storage device of claim 27, wherein translation of the body relative to the fixed plate is guided by a pair of spaced guides.

30. The defibrillator device of claim 27, further comprising a heating device disposed within the housing in proximity of the automated external defibrillator to transfer radiant heat thereto.

31. The defibrillator device of claim 27, further comprising a heating plate pivotally attached along a bottom edge thereof to the bottom edge of the housing inward of the door, the heating plate dimensioned to cover at least a portion of the automated external defibrillator to transfer radiant heat thereto.

32. The defibrillator device of claim 27, further comprising a movable partition disposed within the housing defining a pocket for receiving the automated external defibrillator therein, the movable partition movable relative to a back wall of the housing and extending upward a predetermined distance from a floor of the housing.

33. The defibrillator device of claim 27, wherein the alarm comprises an electrical circuit and a battery.

34. The defibrillator device of claim 27, wherein alarm activation is independent of door movement.

* * * * *